(12) United States Patent
Abdolahad et al.

(10) Patent No.: US 10,775,336 B2
(45) Date of Patent: Sep. 15, 2020

(54) ELECTROMECHANICAL APPROACH FOR CANCER DETECTION

(71) Applicants: Mohammad Abdolahad, Tehran (IR); Ali Saeidi, Tehran (IR); Milad Gharooni, Tehran (IR)

(72) Inventors: Mohammad Abdolahad, Tehran (IR); Ali Saeidi, Tehran (IR); Milad Gharooni, Tehran (IR)

( * ) Notice: Subject to any disclaimer, the term of this patent is extended or adjusted under 35 U.S.C. 154(b) by 346 days.

(21) Appl. No.: 15/238,795

(22) Filed: Aug. 17, 2016

(65) Prior Publication Data

US 2016/0356739 A1 Dec. 8, 2016

Related U.S. Application Data

(60) Provisional application No. 62/263,616, filed on Dec. 5, 2015.

(51) Int. Cl.
| | |
|---|---|
| *G01N 27/327* | (2006.01) |
| *G01N 33/483* | (2006.01) |
| *G01N 27/28* | (2006.01) |
| *C25F 3/08* | (2006.01) |
| *C23C 28/00* | (2006.01) |
| *C23C 14/16* | (2006.01) |
| *G01N 27/02* | (2006.01) |

(52) U.S. Cl.
CPC ......... *G01N 27/3278* (2013.01); *C23C 14/16* (2013.01); *C23C 28/321* (2013.01); *C23C 28/322* (2013.01); *C23C 28/34* (2013.01); *C25F 3/08* (2013.01); *G01N 27/283* (2013.01); *G01N 33/4833* (2013.01); *G01N 27/028* (2013.01)

(58) Field of Classification Search
CPC ............. G01N 27/3278; G01N 27/028; G01N 27/283; G01N 33/4833; C23C 14/16; C23C 28/322; C23C 28/321; C23C 28/34
See application file for complete search history.

(56) References Cited

U.S. PATENT DOCUMENTS

| | | | |
|---|---|---|---|
| 8,070,929 B2 * | 12/2011 | Kim | ........................ B01J 23/28 205/118 |
| 9,151,759 B2 | 10/2015 | Matsui et al. | |
| (Continued) | | | |

OTHER PUBLICATIONS

Abdolhad et al. A single-cell correlative nanoelectromechanosensing approach to detect cancerous transformation: monitoring the function of F-acting microfilaments in the modulation of the ion channel activity. Nanoscale. Royal Society of Chemistry. vol. 7 pp. 1879-1886. 2015. (Year: 2015).*

(Continued)

*Primary Examiner* — Michael L Hobbs
(74) *Attorney, Agent, or Firm* — Bajwa IP Law Firm; Haris Zaheer Bajwa

(57) ABSTRACT

An electrical probe is disclosed for measuring an electrical response from a biological cell. The electrical probe includes a tungsten microwire having a sharpened tip section, a catalyst layer formed on the sharpened tip section of the tungsten microwire, and an array of nanotube electrodes vertically aligned on the catalyst layer. The catalyst layer includes a catalyst bilayer including a nickel layer over a gold layer, and the nanotube electrodes include a plurality of silicon nanotubes (SiNTs).

2 Claims, 28 Drawing Sheets

(56) References Cited

U.S. PATENT DOCUMENTS

2004/0113621 A1* 6/2004 Naughton .............. G01Q 60/52
324/321
2006/0228287 A1* 10/2006 Zettl ...................... B82Y 30/00
423/447.1
2008/0140195 A1* 6/2008 Su ...................... A61B 5/04001
623/11.11
2016/0372271 A1* 12/2016 Kitagawa ............. H01G 9/2027

OTHER PUBLICATIONS

K. Enomoto, Mechanically induced electrical and intracellular calcium responses in normal and cancerous mammary cells, 1992, Cell calcium, vol. 13, Issue 8, pp. 501-511.

* cited by examiner

ELECTROMECHANICAL APPROACH FOR CANCER DETECTION

CROSS REFERENCE TO RELATED APPLICATION

The present application claims priority from U.S. Provisional Patent Application Ser. No. 62/263,616, filed Dec. 5, 2015, entitled "A SINW-ECIS BIOSENSOR", which is incorporated by reference herein in its entirety.

TECHNICAL FIELD

The present disclosure generally relates to a tungsten (W) supported silicon nanotube (SiNT) based electrical probe (designated hereinafter as "SiNT/W probe"), a method for fabrication thereof, and applications thereof in detecting cancerous state of a single cell.

BACKGROUND

Cancer is recognized as a type of disease that affects many biochemical, electrical, and mechanical functions of a cell. Cytoskeletal alterations, damping of electrodynamic microtubule oscillations, diminution of dielectric properties of the membrane, and disruption in the ion channel activity are some of the considerable mechanical and electrical alterations in cells during cancerous transformation.

Highly accurate methods for monitoring such alterations in single cells, such as electrical, mechanical, and electro-optical monitoring of single cells may detect cancerous transformation in its early stages. In case of electrical recording, high spatial resolution contacts between electrical probes and single cells and also non-invasive recording are critical for both fundamental biophysical studies and disease monitoring; particularly for bioelectrical signals, which are weaker than action potentials.

Nanoscale electrical probes (e.g., conductive silicon nanowires and silicon nanotubes (SiNT)) have opened new fields of investigation, leading to the emergence of possible future applications in cell bioelectrical and electrophysiological studies. Recently, the nanostructured probe-based electrical recording methods have been applied solely for action potential measurements outside the cell of some special types of electrically active cells with sharp responses, such as neurons and cardiomyocytes.

Therefore, there is a need for a label-free cancer diagnosis or cancer progression detection method with single-cell resolution using non-invasive devices or instruments capable of measuring intracellular bioelectrical responses, even minor electrical variations for a wide range of cell types.

SUMMARY

In one general aspect of the present disclosure, an electrical probe for measuring an electrical response from a biological cell is disclosed. The probe includes a microwire having a sharpened tip; a catalyst layer formed on the sharpened tip of the microwire; and an array of nanotube electrodes vertically aligned on the catalyst layer. The array of nanotube electrodes are configured to measure an electrical response of a biological cell in contact with the electrodes.

The above general aspect may include one or more of the following features. The microwire may include a tungsten microwire with a diameter less than about 2000 µm having a sharpened tip with a diameter about 200 nm. The catalyst layer may include a bilayer having a Nickel layer (Ni) with a thickness of about 10 nm to about 40 nm and a Gold layer (Au) with a thickness of about 1 nm to about 4 nm. The nanotube electrodes may include a plurality of silicon nanotubes (SiNTs).

In another general aspect of the present disclosure, a method for fabricating a SiNT/W probe is described. The exemplary method may include the steps of sharpening one end of a tungsten (W) microwire to form a tungsten (W) needle having a sharp pointed tip, cleaning the tungsten (W) needle to form a cleaned tungsten (W) needle, forming a catalyst bilayer on the sharp tip of the cleaned tungsten (W) needle, growing a plurality of silicon nanotubes (SiNTs) on the catalyst bilayer to form a SiNT/W needle, transferring the SiNT/W needle into a doping furnace to form a doped conductive SiNT/W needle, and coating a gold layer on top of the SiNTs of the doped conductive SiNT/W needle to form a SiNT/W probe. The electrical probe is configured to measure an electrical response of a biological cell contacting the silicon nanotubes (SiNTs).

In one exemplary implementation, the one end of a tungsten (W) microwire may be sharpened through an electrochemical etching process. The tungsten (W) needle may be cleaned via immersion in a solution, for example a solution of acetone and buffer HF. The catalyst bilayer on the sharp tip of the cleaned tungsten (W) needle may be formed via a two-step deposition process using an electron beam coating system. The two-step deposition process may include steps of: holding the cleaned tungsten (W) needle under a gold plume to coat a layer of gold on the sharp tip to form a first catalyst layer and holding the cleaned tungsten (W) needle having the first catalyst layer under a nickel plume to coat a layer of nickel over the first catalyst layer to form the catalyst bilayer (Ni—Au) on the sharp tip of the cleaned tungsten (W) needle. The plurality of SiNTs can be grown via a vapor-solid-liquid (VLS) process using a Low-Pressure Chemical Vapor Deposition (LPCVD) system. The doping furnace may include a phosphorous doping furnace. The gold layer may be coated on top of the SiNTs of the doped conductive SiNT/W needle by assistance of a sputtering system.

In another general aspect of the present disclosure, a single-cell-based electromechanical method for cancerous state detection is described. The exemplary method includes the steps of: preparing a suspension of individually suspended biological cells, extracting a single cell from the suspension, holding the extracted single cell from the suspension, measuring a first electrical response of the held single cell, step-wised mechanical aspirating the held single cell to form a mechanically deformed cell; and measuring an electrical response of the held single cell after each step of mechanical aspirating. The cancerous state of the single cell is determined based on the changes in the measured electrical responses.

In one exemplary implementation, the biological cells include biological cells having an elastic cell membrane.

In some exemplary implementations, the suspension of individually suspended biological cells may be prepared through steps of culturing a plurality of biological cells onto a substrate, washing the cultured cells, trypsinizing the cultured cells to detach the cultured cells from the substrate and form a solution, and centrifuging the solution to separate a cell suspension including individually suspended biological cells.

In some exemplary implementations, the single cell may be extracted and held by assistance of an electrically activated micropipette. The electrically activated micropipette may include a glass micropipette coated with an electrically conductive layer, particularly a gold layer having a specific thickness of about 10 nm.

In some exemplary implementations, the electrical response of the held single cell may be measured by assistance of an electrical probe. The electrical probe includes tungsten-(W—) supported silicon nanotube-(SiNT-) based (SiNT/W) electrical probe.

In another exemplary aspect of the present disclosure, an electromechanical system for detecting cancerous state of a single cell is described. The exemplary system includes an aspirating mechanism and an electrical measurement mechanism. The aspirating mechanism may be configured to extract and hold a single cell and apply a mechanical aspiration to the single cell, and the electrical measurement mechanism may be configured to measure an electrical response of the single cell. The cancerous state of the single cell may be detected based on the changes of the measured electrical responses.

In some exemplary implementations, the aspirating mechanism may include an electrically activated glass micropipette coated with a gold layer and having two ends. The electrically activated glass micropipette may be assembled on a microinjection microscope from one end and having a nozzle at the other end, the nozzle may be configured to apply and transfer the mechanical aspiration.

In some exemplary implementations, the electrical measurement mechanism may include an electrical probe, configured to connect to the extracted and held single cell, a signal controlling system, configured to apply an electrical signal to the extracted and held single cell connected to the electrical probe and to acquire an electrical response corresponding to the electrical signal from the extracted and held single cell connected to the electrical probe; and a data processor, configured to record and analyze the electrical response to detect the cancerous state of the single cell.

In some implementations, the electrical probe may include a tungsten-supported silicon nanotube-based (SiNT/W) probe.

In some implementations, the signal controlling system may include an AC signal source configured for applying the electrical signal to the electrical probe, and a data acquisition module configured for acquiring the electrical response corresponding to the electrical signal from the electrical sensors. In some exemplary implementations, the AC signal source may apply a voltage of about 40 mV to the electrical sensors. Correspondingly, the applied voltage may have a frequency in a range of about 100 Hz to 100 KHz.

DETAILED DESCRIPTION

The following detailed description is presented to enable a person skilled in the art to make and use the methods and systems disclosed in exemplary embodiment of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown, but is to be accorded the widest possible scope consistent with the principles and features disclosed herein.

Disclosed herein is an exemplary nanostructured electrical probe (a tungsten-(W—) supported silicon nanotube- (SiNT-) based electrical probe (SiNT/W probe)) and an exemplary method for fabrication thereof. The probe may be considered for a non-invasive measurement of electrical responses of a cell.

In an aspect, the present disclosure describes an exemplary electromechanical method to detect changes in the electrical properties of a single cell, between normal and cancerous states during a mechanical deformation. The method is based on the role of actin microfilaments within a cell in modulation of the ion channel activity and consequently based on the electrical response (e.g. electrical impedance, phase, etc.) of a cell during a mechanical deformation, such as mechanical aspiration. In some aspects, the method may be considered as a new label-free electromechanical cancer diagnosis and cancer progression monitoring method with a single-cell resolution.

Figure 1:
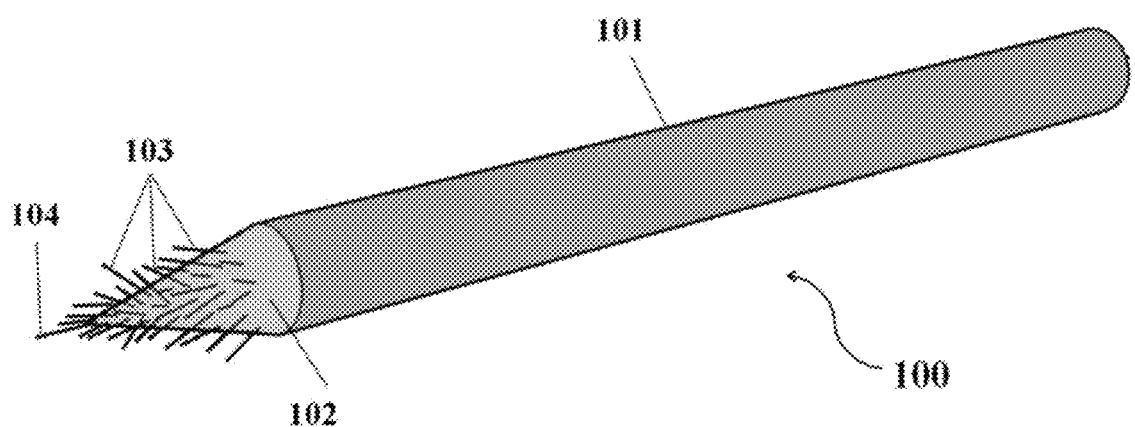
FIG. 1 is a schematic of one example of a SiNT/W probe, consistent with one or more exemplary embodiments of the present disclosure.

FIG. 1 illustrates a schematic of one example of a SiNT/W probe 100, consistent with one or more exemplary embodiments of the present disclosure, which may be configured for measuring an electrical response from a biological cell. Referring to the implementation shown in FIG. 1, the SiNT/W probe 100 may include a tungsten (W) microwire 101 with a sharpened tip section 102 that may be coated with a catalyst bilayer and a plurality of silicon nanotube (SiNTs) electrodes 103 vertically aligned on the catalyst bilayer. The SiNTs 103 may be configured to connect or attach to a biological cell and measure an electrical response of the biological cell that is in contact with the electrodes. Accordingly, a long free-end SiNT 104 may be used among other SiNTs within the array. The long free-end SiNT 104 may be configured for connecting to a biological cell and penetrating the biological cell for further electrical measurement purposes according to one or more aspects of the present disclosure.

As used herein, a microwire may be a fine wire with a circular cross-section and a diameter less than 2000 μm. The microwire 101 may be, for example a tungsten (W) microwire. In certain examples, the tungsten (W) microwire 101 may have a diameter less than about 500 μm. A sharpened tip of the sharpened tip section 102 of the tungsten (W) microwire where the long free-end SiNT 104 may be connected may have a diameter of about 200 nm.

In some exemplary implementations, the catalyst layer may include a catalyst bilayer. The catalyst bilayer, as used herein, is defined as a double-layered catalyst with one layer of a first catalyst coated on another layer of a second catalyst. The catalyst bilayer may include a layer of Nickel (Ni) with a thickness of, for example about 10 nm to about 40 nm over a layer of gold (Au) with a thickness of, for example about 1 nm to about 4 nm forming a catalyst bilayer (Ni—Au).

In an implementation, the array of nanotubes 103 may include a plurality of vertically-aligned silicon nanotubes (SiNTs) that may be grown on the catalyst bilayer. The SiNTs may have a thickness or diameter of, for example less than about 100 nm.

Figure 2:
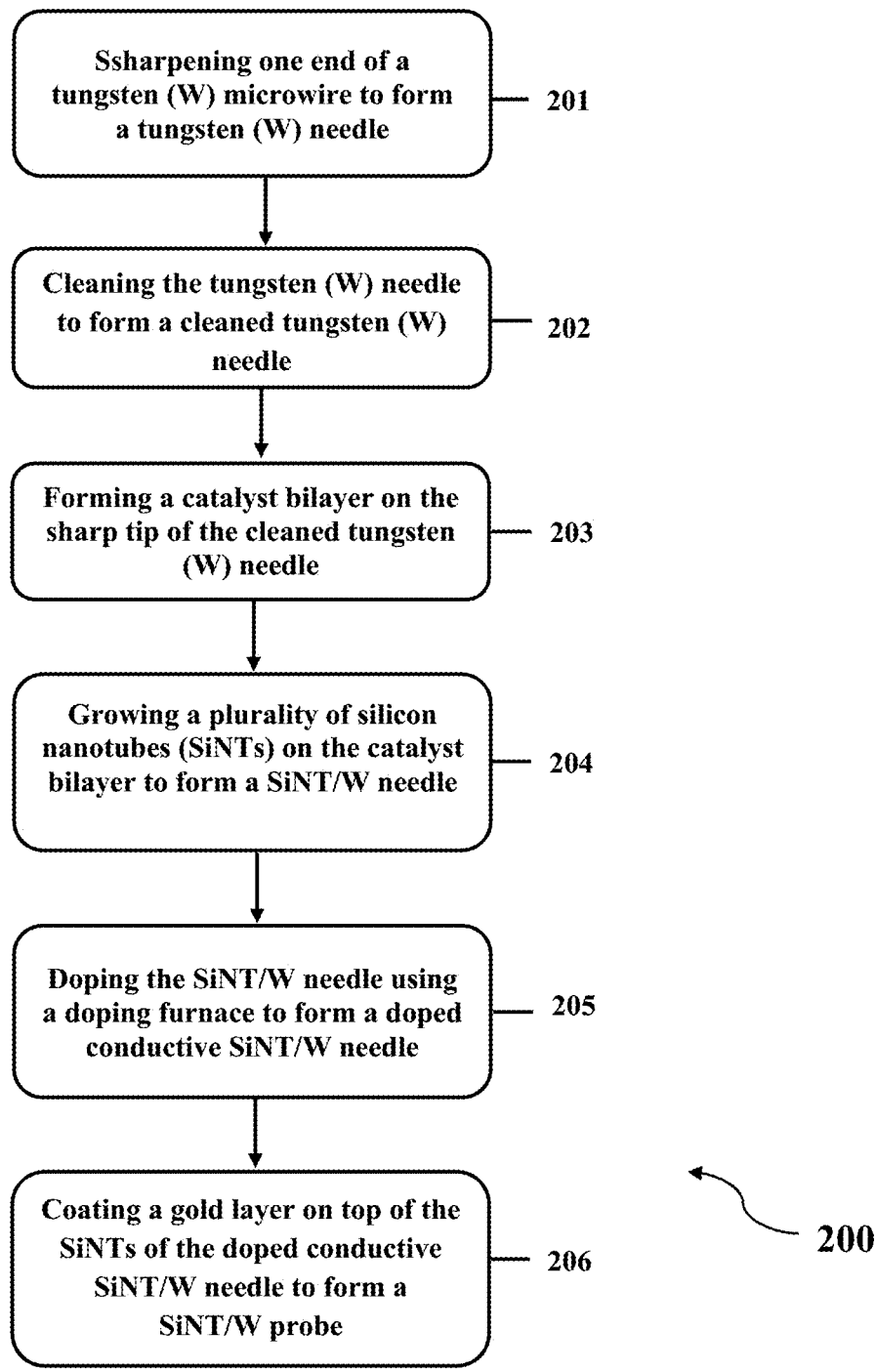
FIG. 2 illustrates an example method for fabricating a SiNT/W probe, consistent with one or more exemplary embodiments of the present disclosure.

FIG. 2 illustrates an example of a method 200 for fabricating the SiNT/W probe 100, consistent with one or more exemplary embodiments of the present disclosure. The method 200 may include the steps of: first, sharpening one end of a tungsten (W) microwire to form a tungsten (W) needle having a sharp pointed tip (step 201), second, cleaning the tungsten (W) needle to obtain a cleaned tungsten (W) needle (step 202), third, forming a catalyst bilayer on the sharpened tip of the cleaned tungsten (W) needle (step 203), fourth, growing a plurality of silicon nanotubes (SiNTs) on the catalyst bilayer to form a SiNT/W needle (step 204), fifth, doping the SiNT/W needle using a doping furnace to form a doped conductive SiNT/W needle (step 205), and sixth, coating a gold layer on top of the SiNTs of the doped conductive SiNT/W needle (step 206).

Figure 3:
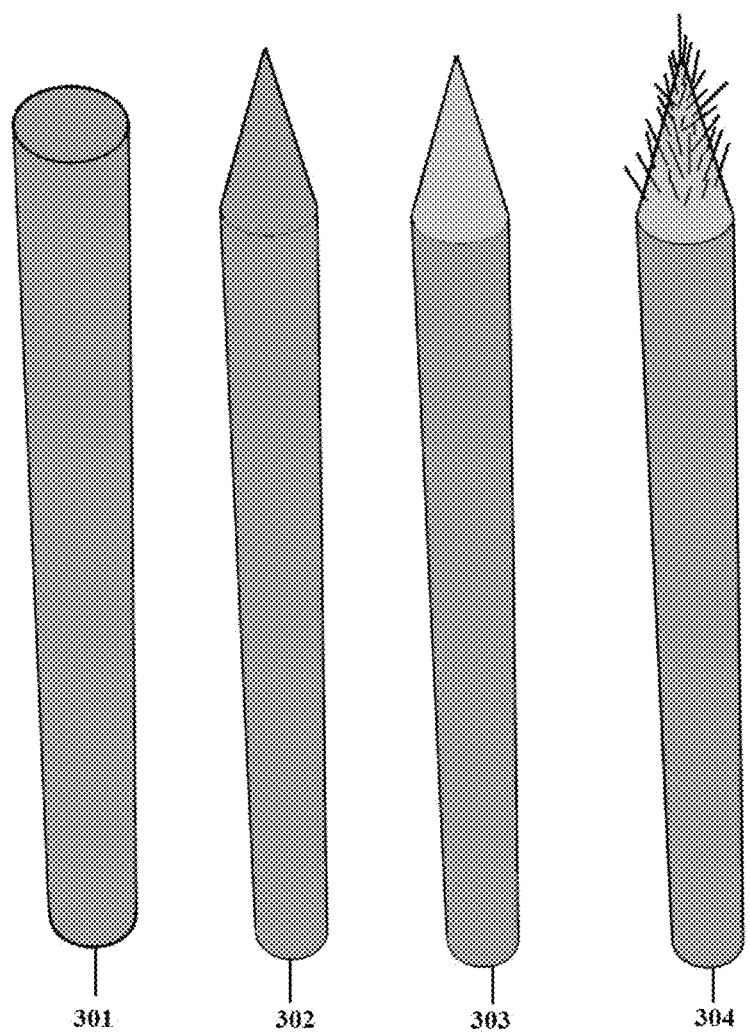
FIG. 3 is a schematic of one example of a tungsten (W) microwire, a tungsten (W) needle, and a cleaned tungsten (W) needle with a catalyst bilayer on the sharp tip and a SiNT/W needle, consistent with one or more exemplary embodiments of the present disclosure.

Referring to the first step 201, an initially supplied tungsten (W) microwire may be sharpened from one end, for example via an electrochemical etching process to form a tungsten (W) needle having a sharp pointed tip. FIG. 3 shows four schematics of one example of the initially supplied tungsten (W) microwire 301, the tungsten (W) needle 302, and the cleaned tungsten (W) needle having a catalyst bilayer on the sharp tip 303 and the SiNT/W needle 304 during the fabrication process, consistent with one or more exemplary embodiments of the present disclosure. Referring to FIG. 3, a schematic of one example of a tungsten (W) microwire 301 and the obtained tungsten (W) needle 302 after step 201 is illustrated.

Moving on to the second step 202, cleaning the tungsten needle may be carried out with immersing the tungsten needle in a cleaning solution, for example, a solution of acetone and buffer HF.

Moving on to the third step 203, the catalyst bilayer may be formed via a two-step deposition process, using, for example, an electron beam coating system via placing the needle in a position in which the top of the needle can be located in front of a target plume. The formation of the catalyst bilayer may include two steps of: first, holding the cleaned tungsten needle under a gold plume to coat a layer of gold on the sharp tip to form a first catalyst layer; and second, holding the cleaned tungsten needle having the first catalyst layer under a Nickel plume to coat a layer of nickel over the first catalyst layer to yield a catalyst bilayer (Ni—Au). Accordingly, a thin layer of gold, with a thickness ranging, for example from about 1 nm to about 4 nm may be coated on top of the sharp tip. Subsequently, a layer of nickel with a thickness ranging, for example from about 10 nm to about 40 nm may be coated over the gold layer. Referring to FIG. 3, a schematic of a tungsten needle 303 having a catalyst bilayer formed over its sharpened tip is illustrated.

Moving on to the fourth step 204, the SiNTs may be grown via a vapor-solid-liquid (VLS) process using a low-pressure chemical vapor deposition (LPCVD) chamber. The VLS process may be carried out by the assistance of, for example $H_2$ and $SiH_4$ gases at a temperature in a range of about 400° C. to about 600° C. and at a pressure of about 1 mTorr. An example of the obtained SiNT/W needle 304 from step 204 is schematically illustrated in FIG. 3.

Moving on to the fifth step 205, the doping step may be carried out by an element of group five of the periodic table, for example, phosphorous. In an implementation, the doping step may be carried out in a phosphorous doping furnace. The SiNT/W needle may be held in the phosphorous doping furnace at a temperature of, for example about 700° C. for about 10 minutes.

Moving on to the final step 206, the gold layer may be coated over the SiNTs via a sputtering system. The thickness of the gold layer may be, for example about 5 nm.

In another aspect, a single-cell-based electromechanical method for cancerous state detection of a single biological cell is described. The biological cell may be a biological cell having an elastic cell membrane with a defined membrane elasticity, for example, epithelial, endothelial, or mesenchymal cells. This method may be used, for example, for cancer diagnosis, detecting cancer transformation or progression, detecting cancer cells among biological cells, investigating metastatic stage, or generally for cancerous state determination of a malignant tissue.

Figure 4:
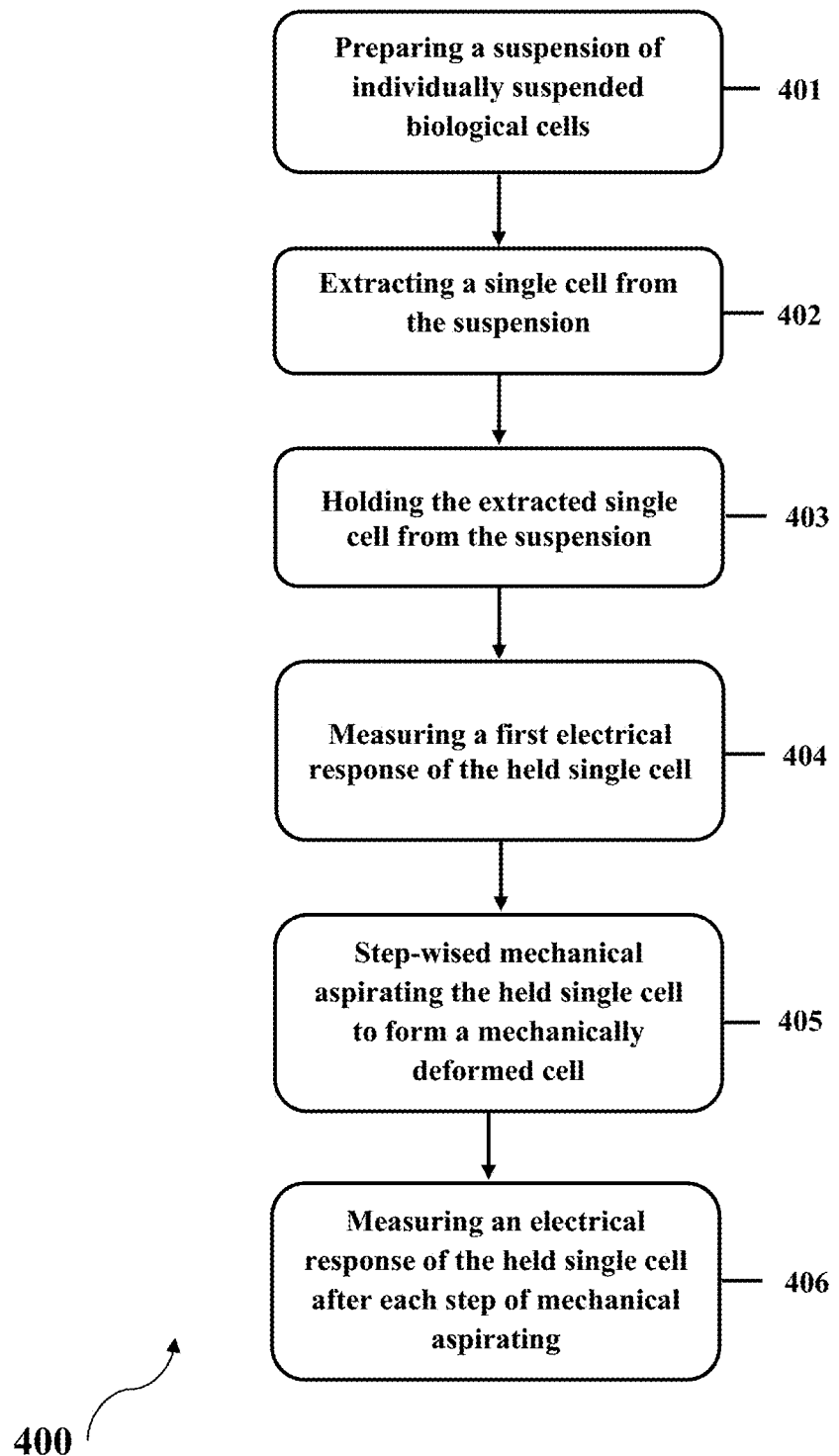
FIG. 4 illustrates an example of a single-cell-based electromechanical method for cancerous state detection, consistent with one or more exemplary embodiments of the present disclosure.

FIG. 4 shows an example of a method 400 for detecting the cancerous state of a single biological cell, consistent with one or more exemplary embodiments of the present disclosure. The method 400 may include steps of first, preparing a suspension of individually suspended biological cells (step 401), second, extracting a single cell from the suspension (step 402), third, holding the extracted single cell from the suspension (step 403), fourth, measuring a first electrical response of the held single cell (step 404), fifth, step-wised mechanical aspirating the held single cell to form a mechanically deformed cell (step 405), and sixth, measuring an electrical response of the held single cell after each step of the mechanical aspirating (step 406).

In step 401, a suspension of biological cells including individual cells that are distributed within the suspension may be prepared via a process with steps of, culturing a plurality of biological cells onto a substrate, washing the cultured cells, trypsinizing the cultured cells to detach the cultured cells from the substrate and form a solution, and centrifuging the solution to separate a cell suspension that includes individually suspended biological cells. Accordingly, a plurality of biological cells may be cultured onto a substrate, for example a glass substrate. The cells may be cultured in a culture medium, for example, a Roswell Park Memorial Institute-1640 (RPMI-1640) medium. The culture medium may be supplemented with a serum-supplement, for example, Fetal bovine serum (FBS) including Fetal bovine with an amount of about 5% and the culture medium may be further supplemented with an antibiotic, for example, penicillin/streptomycin with an amount of about 1%. Then, the cultured cell may be washed with a buffer solution, for example, a Phosphate-buffered saline (PBS) solution to remove the remained cultured media and supplements from the cultured cells. Subsequently, the cultured and washed cells may be trypsinized by assistance of adding a solution including trypsin and EDTA to the cultured cells in order to detach the cultured cells from the substrate and form a solution including the cells. Finally, the obtained solution including the cultured cells may be centrifuged to discard the trypsinizing solution and separate a cell suspension including individually suspended biological cells.

Referring to second step 402 and subsequently, third step 403, a single cell may be extracted from the suspension and held for a while by assistance of an electrically activated micropipette. The electrically activated micropipette may be a glass micropipette with a diameter in a range of about 4.5 μm to about 5 μm, which may be coated with an electrically conductive layer, for example, a gold (Au) layer. The gold (Au) layer may be coated with a thickness of, for example about 10 nm over the glass micropipette via, for example a sputtering system.

Moving on to step 404, an electrical response of the held cell, for example, an electrical impedance of the cell membrane of the held cell may be measured using an electrical probe connected to the cell. The electrical probe may include a SiNT/W probe, designed and fabricated pursuant to the teachings of the present disclosure.

Moving on to step 405, the held single cell may be aspirated by assistance of the same electrically activated micropipette, which was used before for extracting step 402 and holding step 403. The electrically-activated micropipette may be assembled on a microinjection microscope to supply the electrically activated micropipette displacements needed in steps 402 and 403. In addition, the negative and positive pressure for aspirating the single cell may be applied to the glass micropipette by assistance of a movable water reservoir of the microinjection microscope. Displacing the water reservoir up or down leads to a suitable pressure to pull in or force away the cell. Furthermore, a micromanipulator may be utilized to adjust each micropipette position. Also, the aspirated leading edge of the cell surface may be monitored using an inverted microscope equipped with a digital camera assembled on the microinjection microscope.

Moving on to step 406, an electrical response of the held single cell after each step of mechanical aspirating of step 405 may be measured. Then, the cancerous state of the single cell may be determined based on the changes of the electrical response measured in step 404 and the electrical responses measured in step 406. Since, the electrical properties of a normal or healthy cell, for example electrical impedance of the cell membrane may be affected significantly by the mechanical properties of the cell, sharp and significant changes in the measured electrical responses from the single cell after cell mechanical deformation may indicate that the extracted single cell from the suspension is a healthy cell. While, no or small alterations in electrical responses measured during mechanical deformation may indicate that the selected and processed single cell via the method 400, pursuant to the teachings of the present disclosure is a cancer cell.

Figure 5A:
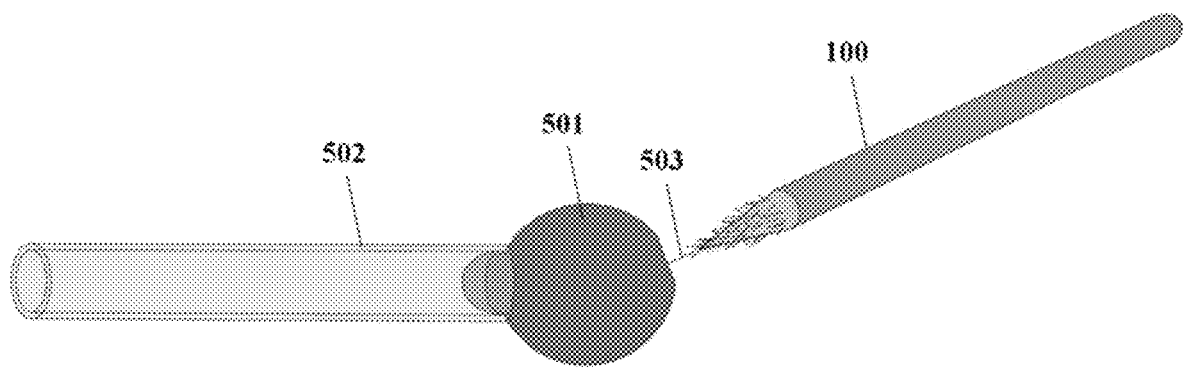
FIG. 5A is a schematic of an example single biological cell held and aspirated by assistance of an electrically activated micropipette and connected to a SiNT/W probe, consistent with one or more exemplary embodiments of the present disclosure.

FIG. 5A shows a schematic of an example of a single biological cell 501, which is extracted from a suspension including individually suspended cells, consistent with one or more exemplary embodiments of the present disclosure. Cell 501 is held and aspirated by assistance of an electrically activated micropipette 502 and it is in contact with a silicon nanotube (SiNT) 503 of a SiNT/W probe similar to a silicon nanotube (SiNT) 104 described hereinabove. SiNT 503 is a long free-end SiNT among the SiNTs array that is formed over the sharpened tip of the probe.

It should be understood that the structure changes in actin microfilament network of a cell due to a mechanical force may be a criterion for diagnosis between cancerous and healthy cells as well as between benign and metastatic cells. For example, a mechanical aspiration mechanism applied on a healthy or benign cell may cause a significant alteration in actin microfilament configuration and subsequently a significant change in an electrical response of the cell, for example electrical impedance or phase. While, a similar mechanical aspiration may not cause any observable change in such electrical responses in case of a cancerous or metastatic cell.

Figure 5B:
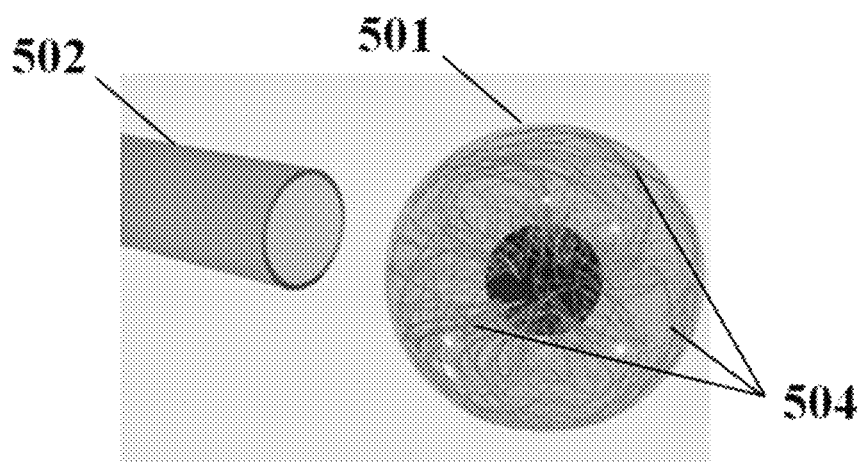
FIG. 5B is a schematic of actin microfilament distribution for an example of a non-aspirated cell, consistent with one or more exemplary embodiments of the present disclosure.
Figure 5C:
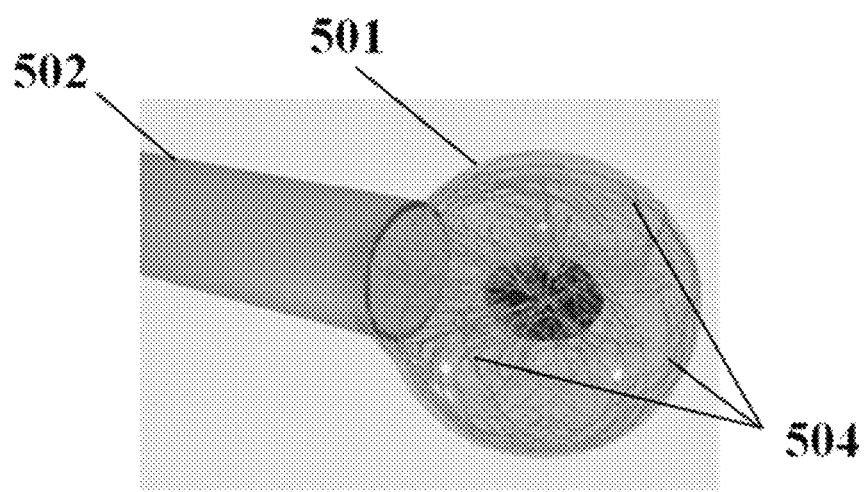
FIG. 5C is a schematic of actin microfilament distribution for an example of an aspirated cell, consistent with one or more exemplary embodiments of the present disclosure.

Accordingly, FIG. 5B shows a schematic of the actin microfilament configuration and distribution for a non-aspirated cell illustrating the electrically activated micropipette 502 near the single cell 501 as described hereinabove and a schematically actin microfilament distribution 504 of the cell, consistent with one or more exemplary embodiments of the present disclosure. Correspondingly, FIG. 5C shows a similar schematic actin microfilament configuration and distribution for an aspirated cell, consistent with one or more exemplary embodiments of the present disclosure.

In another aspect, an electromechanical system for detecting cancerous state of a single cell is described. The system may include a first aspirating mechanism to extract and hold a single cell and apply a mechanical aspiration to the single cell; and a second electrical measurement mechanism to measure an electrical response of the single cell. The cancerous state of the single cell may be detected based on the changes of the measured electrical responses.

Figure 6:
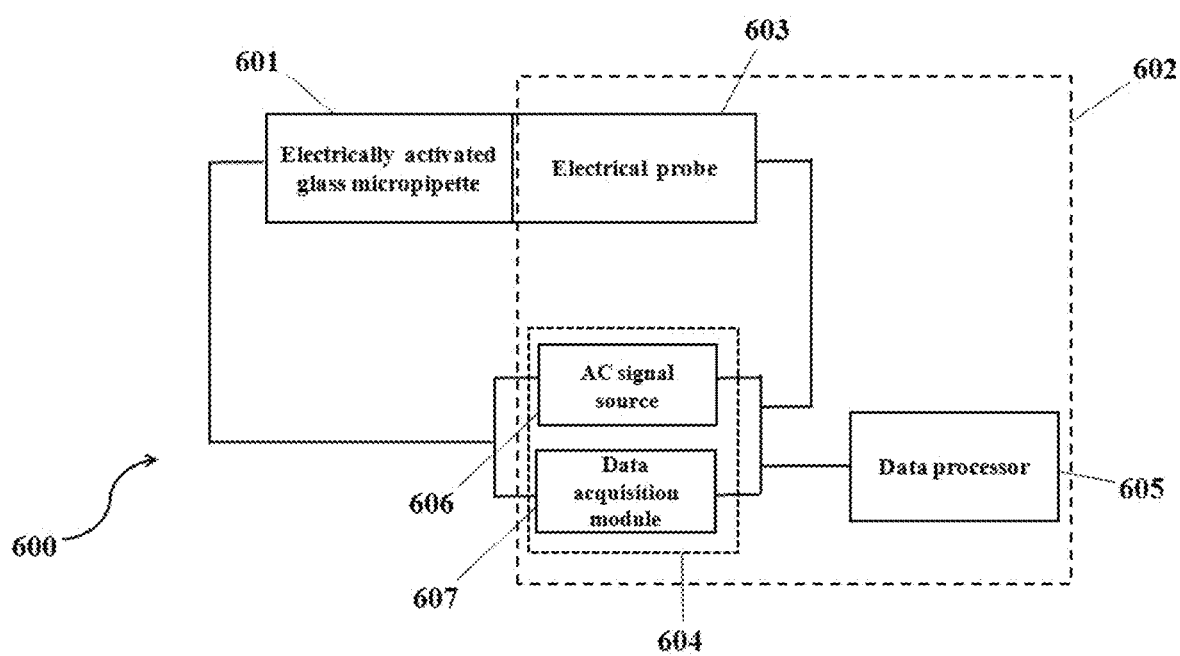
FIG. 6 illustrates an example of an electromechanical system for detecting cancerous state of a single cell, consistent with one or more exemplary embodiments of the present disclosure.

FIG. 6 illustrates an example of an electromechanical system 600, configured to detect cancerous state of a single cell, consistent with one or more exemplary embodiments of the present disclosure. The electromechanical system 600 may be utilized to implement the method 400 of FIG. 4 for detecting cancerous state of a single cell as described above. Exemplary system 600 includes an aspirating mechanism 601 configured to extract and hold a single cell and then applying a mechanical aspiration to the single cell and an electrical measurement mechanism 602 configured to measure an electrical response of the single cell. In an implementation, the aspirating mechanism 601 may include an electrically activated glass micropipette (similar to electrically activated micropipette 502) with two ends, which is coated with a gold layer. The electrically activated glass micropipette may be assembled on a microinjection microscope from one end, while having a nozzle at the other end to apply and transfer the mechanical aspiration to the single cell.

Referring to FIG. 6, the electrical measurement mechanism 602 may include: an electrical probe 603 configured to be connected to the held cell by the electrically activated glass micropipette for electrical measurements; a signal controlling system 604 configured for applying an electrical signal to the extracted and held single cell connected to the electrical probe 603 and acquiring the corresponding electrical response of the extracted and held single cell connected to the electrical probe 603, and a data processor 605 configured for recording and analyzing the electrical response in order to detect the cancerous state of the single cell. The electrical probe 603 may include a tungsten-supported silicon nanotube-based (SiNT/W) probe assembled on a microinjection microscope opposite to the electrically activated glass micropipette 502 to connect and penetrate a long free-end SiNT 503 to the single cell held by the electrically activated glass micropipette.

With further reference to FIG. 6, the signal controlling system 604 may include an AC signal source 606 configured for applying the electrical signal to the electrical probe 603 and a data acquisition module 607 configured for acquiring the electrical response corresponding to the electrical signal from the electrical probe 603. The AC signal source 606 may be configured to apply a voltage of, for example, about 40 mV to the electrical probe 603. Accordingly, the applied voltage may cause a frequency that ranges from about 100 Hz to about 100 KHz.

EXAMPLES

Example 1

Fabricating a SiNT/W Probe

Figure 7A:
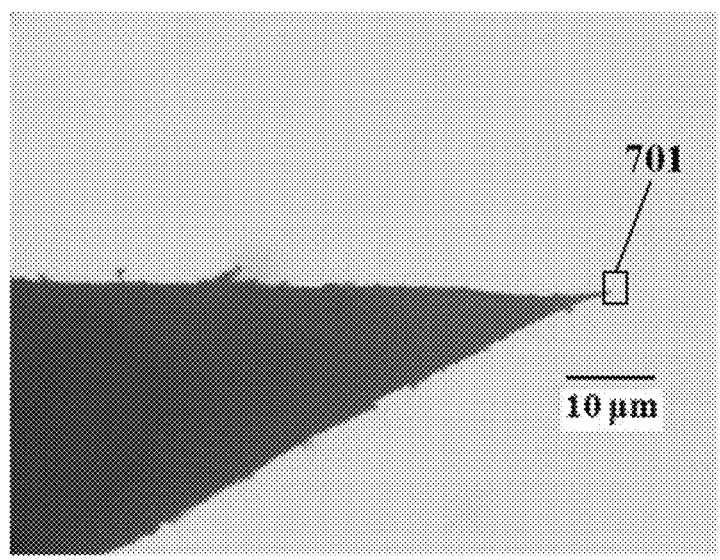
FIG. 7A illustrates an optical image of an example of a sharpened tip of a tungsten (W) needle, consistent with one or more exemplary embodiments of the present disclosure.
Figure 7B:
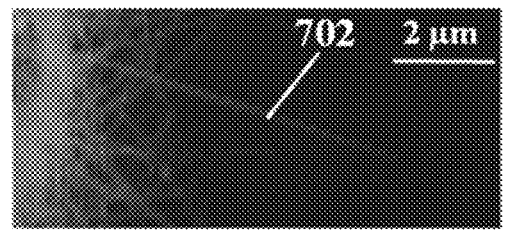
FIG. 7B illustrates a field emission scanning electron microscope (FESEM) micrograph of an example of grown array of SiNTs over the sharpened tip of a W needle, consistent with one or more exemplary embodiments of the present disclosure.
Figure 7C:
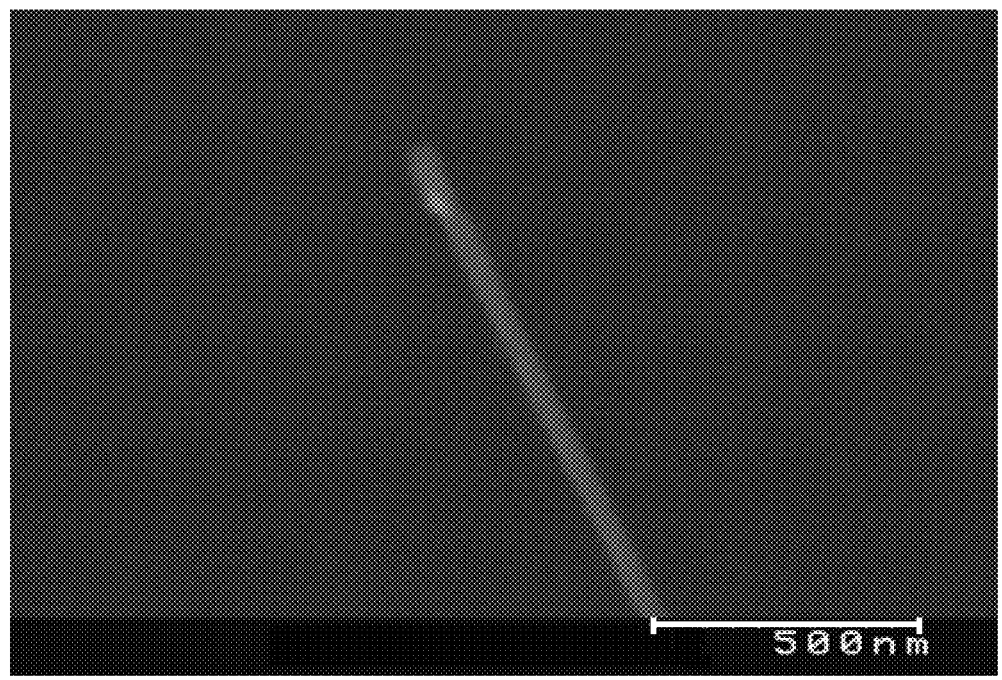
FIG. 7C illustrates a field emission scanning electron microscope FESEM) micrograph of an example of a single long free end silicon nanotube (SiNT) among an array of SiNTs grown over a sharpened tip of a W needle, consistent with one or more exemplary embodiments of the present disclosure.

In this exemplary scenario, a tungsten (W) needle as a support for a SiNT/W probe may be made from an initial W microwire with a diameter of about 500 μm, using an electrochemical etching process. An optical image of an example sharpened tip of a W needle is shown in FIG. 7A, representing the formed tip at one end of the needle with a diameter of about 200 nm. The W needle may be washed and cleaned with a solution of acetone and Buffer HF. Subsequently, the cleaned needle may be held in an electron beam coating system) to deposit a bilayer catalyst of Nickel-Gold (Ni—Au) on the sharp tip of the cleaned W needle. During the deposition process, the needle may be placed in a position in which, the top portion of the needle is located in front of the target plume. The deposition may begin at a base pressure of about $10^{-6}$ Torr. A thin layer of gold, with a thickness of about 2 nm may be coated on the tip of the probe. Subsequently, another layer of nickel with a thickness of about 20 nm may be coated over the gold layer. In a next step, the growth of SiNTs on the catalyst bilayer may be achieved via placing the W needle coated with the Ni—Au catalyst over the tip in a LPCVD chamber (SensIran Co. Iran). The SiNTs may be grown over the catalyst bilayer by the assistance of $H_2$ and $SiH_4$ gases at a base pressure of about 1 mTorr and at a temperature of about 450° C. to form the SiNT/W needle. A magnified zone of FIG. 7A represented by 701 is shown in FIG. 7B. This figure illustrates a field emission scanning electron microscope (FESEM) image of an example grown array of SiNTs over the sharpened tip of a W needle. Then, the SiNT/W needle may be transferred into a phosphorous doping furnace and held at a temperature of about 700° C. for about 10 minutes to enhance the conductivity of the nanotubes by the diffusion of phosphorous dopants atoms. Finally, a gold layer with a thickness of about 5 nm may be coated on top of the nanotubes with the assistance of a sputtering system to form the SiNT/W probe. FIG. 7C illustrates a field emission scanning electron microscope (FESEM) micrograph of an example of a single silicon long free end nanotube (SiNT) 702 of FIG. 7B among the array of SiNTs over the sharpened tip of a W needle, the most appropriate SiNT among the SiNTs array for further superficial and negligibly invasive cell connection and penetration electrical measurement purposes causing the least electrical noises. This figure also shows a diameter of about 70 nm for the formed SiNT on the probe tip.

Example 2

Investigation of the Electrical Sensitivity

In this example, the basic electrical sensitivity of the disclosed system may be characterized by entering and placing a SiNT/W probe and an electrically activated glass micropipette of the system pursuant to the present disclosure in an ionic cellular media solution containing a biological cell suspension, followed by comparing the sensitivity before and after connecting the SiNT/W probe to the cell grasped by the micropipette, and finally by scaling under a dry atmosphere.

Figure 8A:
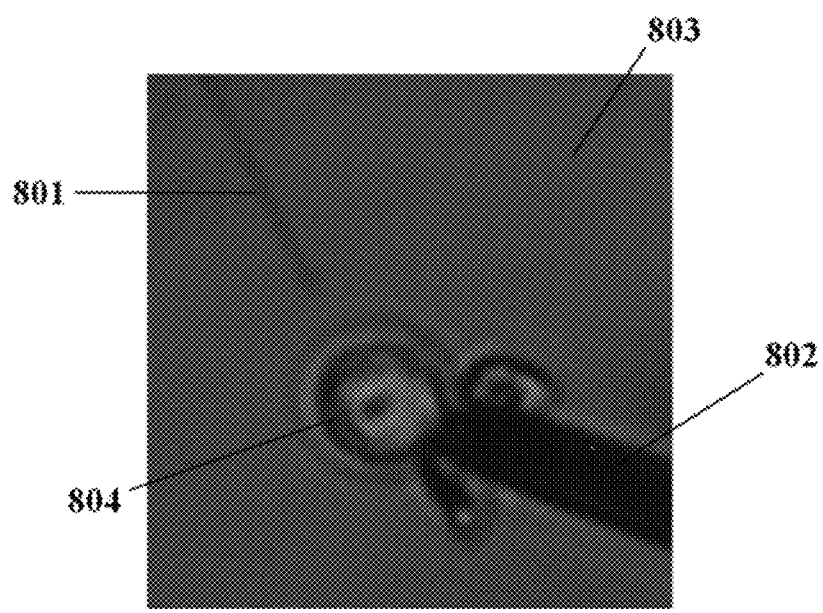
FIG. 8A illustrates an optical image of an example of a single biological cell held by assistance of an electrically activated micropipette and a long free end SiNT of a SiNT/W probe placed in a cellular media solution, consistent with one or more exemplary embodiments of the present disclosure.
Figure 8B:
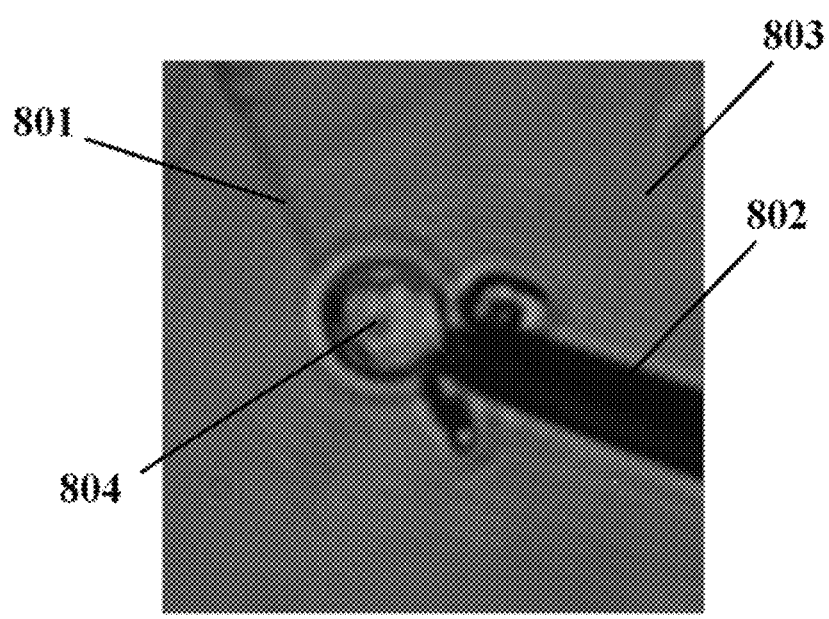
FIG. 8B illustrates an optical image of an example single biological cell held and aspirated by assistance of an electrically activated micropipette and connected to a long free end SiNT of a SiNT/W probe, consistent with one or more exemplary embodiments of the present disclosure.
Figure 8C:
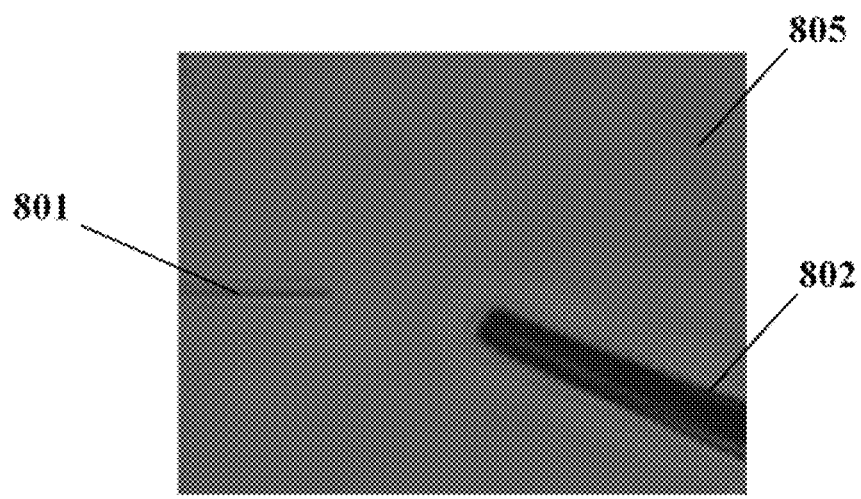
FIG. 8C illustrates an optical image of an example electrically activated micropipette and a long free end SiNT of a SiNT/W probe placed in the air atmosphere, consistent with one or more exemplary embodiments of the present disclosure.

FIGS. 8A-8C show optical images of three situations configured for measurement of the electrical response before (FIG. 8A) and after (FIG. 8B) the connection of the SiNT/W probe to the cell within a cellular media solution and finally in a dry ambient atmosphere (FIG. 8C), consistent with one or more exemplary embodiments of the present disclosure.

Referring to FIG. 8A, an optical image of a long free end SiNT 801 of a SiNT/W probe and an electrically activated micropipette 802 placed in a cellular media solution 803 is illustrated. A single biological cell 804 may be selected and held within the cellular media solution 803 by assistance of the electrically activated micropipette 802, while the probe may be placed over the cell without any connections to the cell. FIG. 8B shows a second situation similar to FIG. 8A, while the long free-end SiNT 801 connected and penetrated the single biological cell 804 aspirated by the electrically activated micropipette 802. Subsequently, FIG. 8C shows a third exemplary situation, in which the long free-end SiNT 801 of a SiNT/W probe and the electrically activated micropipette 802 are placed in a dry air atmosphere 805.

Figure 9A:
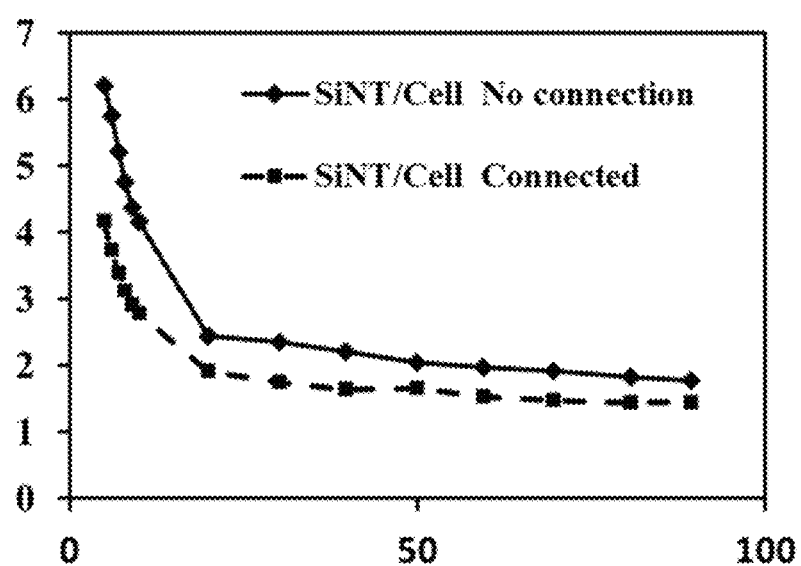
FIG. 9A is an electrical impedance (electrical sensitivity) curve measured in a cellular media solution for a frequency range of about 0 KHz to about 100 KHz in two situations of: SiNT not connected to a single cell (solid line) and SiNT connected to a single cell (dashed line), consistent with one or more exemplary embodiments of the present disclosure.
Figure 9B:
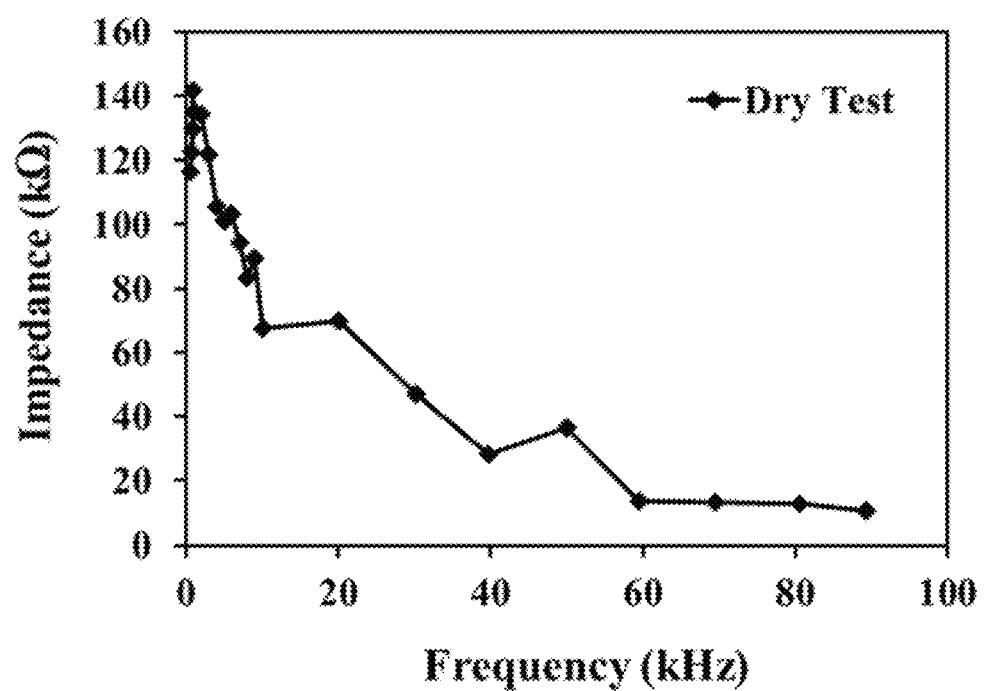
FIG. 9B is an electrical impedance (electrical sensitivity) curve measured in an air atmosphere for a frequency range of about 0 KHz to about 100 KHz, consistent with one or more exemplary embodiments of the present disclosure.

FIGS. 9A and 9B show corresponding electrical impedance (electrical sensitivity) values that are measured in a frequency range of about 0 KHz to about 100 KHz for the three exemplary situations described above and shown in FIGS. 8A-8C, consistent with one or more exemplary embodiments of the present disclosure. Referring to FIG. 9A, representing the impedance values for the first and second situations within the cellular media solution, the impedance curves are obtained for the cases, where the SiNT is not connected to the single cell (designated by the solid line) and where the SiNT is connected to the single cell (designated by the dashed line) are within a similar range of about 1 k$\Omega$ to about 7 k$\Omega$, while regarding FIG. 9B, the impedance magnitudes increased significantly to a range of about 0 k$\Omega$ to about 140 k$\Omega$ when the ambient was changed from a cellular media solution to an air atmosphere in a fixed distance between the SiNT and the micropipette (about 7 μm).

Example 3

Detecting the Cancerous State of a Single Cell

In this example, the electromechanical method and system may be used to detect the cancerous state of a single cell. To this end, healthy lung cells (MRC-5) and cancerous lung cells (QU-DB) were utilized. The MRC-5 was derived from a healthy or normal lung tissue and QU-DB was derived from a human lung carcinoma tissue. For cell culturing, cells were maintained in a $CO_2$ incubator (37° C., 5% $CO_2$, 95% air) in a RPMI-1640 medium supplemented with 5% fetal bovine serum (Gibco), and 1% penicillin/streptomycin (Gibco). The fresh medium was replaced every day. Prior to each experiment, cells were trypsinized in order to be detached from the substrate and were suspended in the culture medium. To minimize the effect of trypsinization, the procedure was carried out in less than 4 minutes at a temperature of about 20-22° C. Single cells suspended within the prepared suspension were extracted, held and aspirated by an electrically activated glass micropipette having a nozzle with an inner diameter of about 5 μm. Then, the SiNT/W probe was connected to the aspirated cell and an electrical response (impedance magnitude and phase) were measured for different suction forces applied by the micropipette.

Figure 10A:
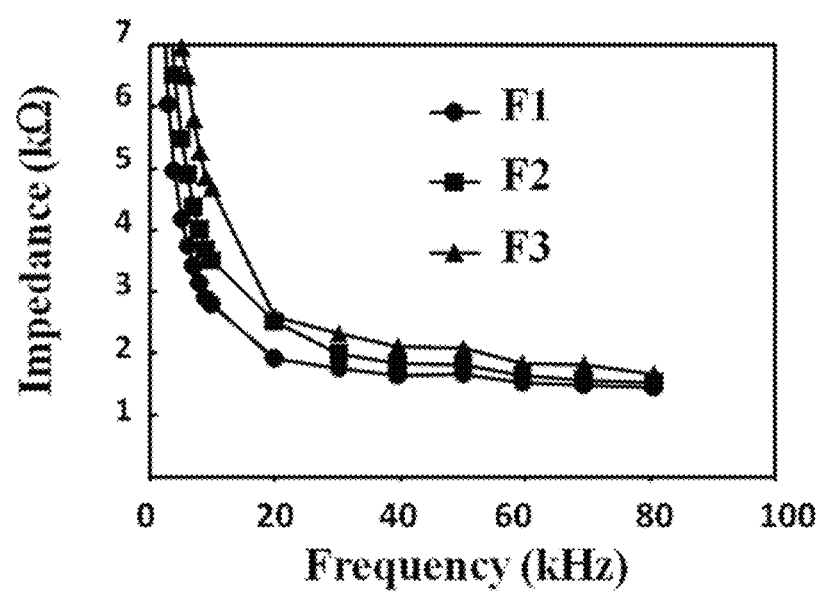
FIG. 10A illustrates a cell impedance versus frequency curve for an example of an aspirated MRC-5 single cell with three different suction amplitudes, consistent with one or more exemplary embodiments of the present disclosure.
Figure 10B:
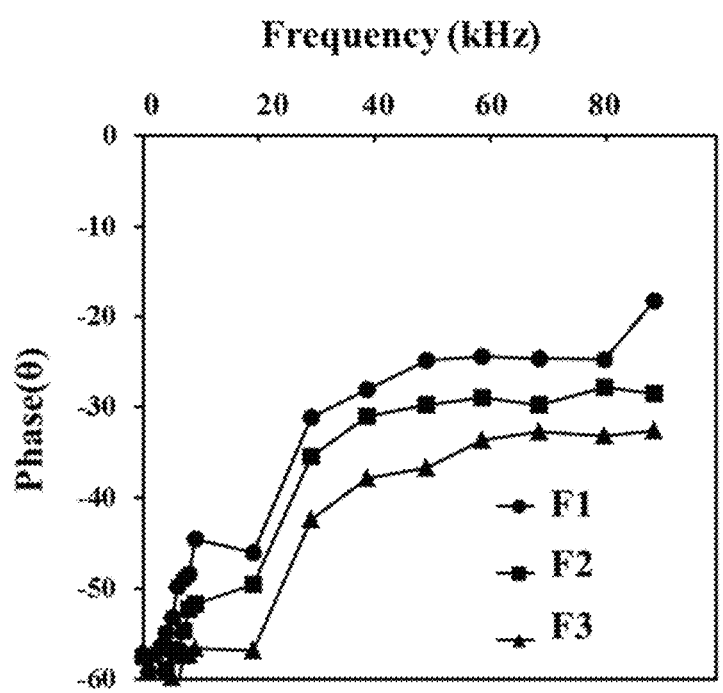
FIG. 10B is a phase response versus frequency curve for an example of an aspirated MRC-5 single cell with three different suction amplitudes, consistent with one or more exemplary embodiments of the present disclosure.
Figure 10C:
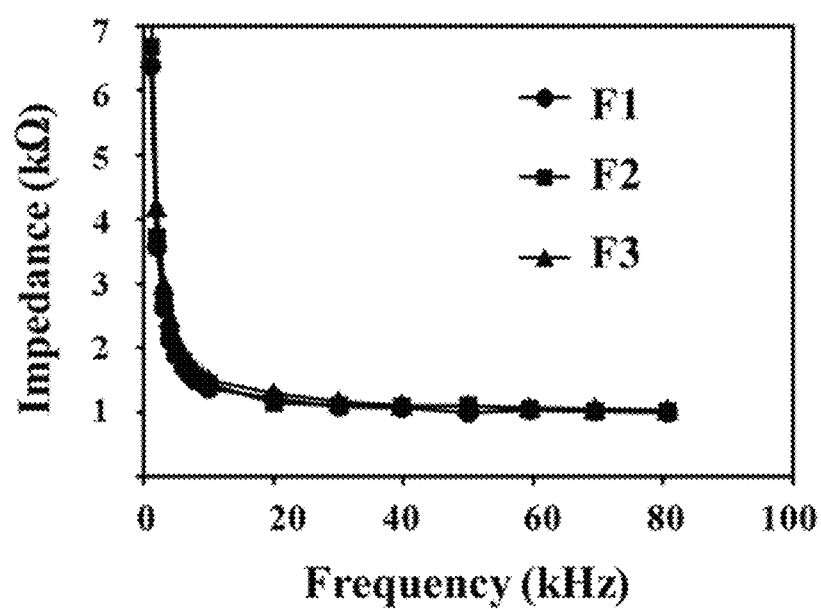
FIG. 10C is a cell impedance versus frequency curve for an example of an aspirated QU-DB single cell with three different suction amplitudes, consistent with one or more exemplary embodiments of the present disclosure.
Figure 10D:
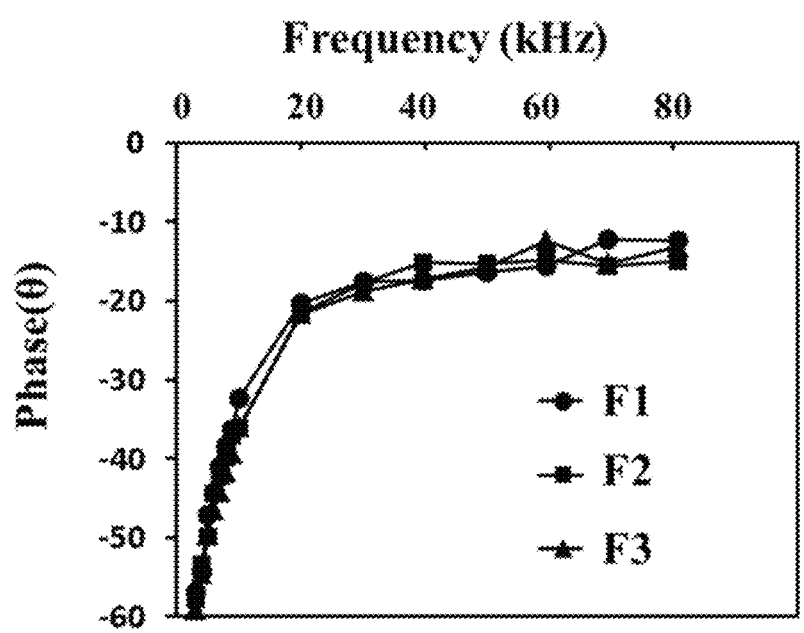
FIG. 10D is a phase response versus frequency curve for an example of an aspirated QU-DB single cell with three different suction amplitudes, consistent with one or more exemplary embodiments of the present disclosure.

FIGS. 10A-10D show the results of the electrical measurements from aspirated MRC-5 and QU-DB cells with various suction forces, consistent with one or more exemplary embodiments of the present disclosure. The representative recorded data in FIGS. 10A and 10B show a clear increase in the cell impedance and phase with increasing mechanical stretch amplitudes from F1 to F3 in healthy cells (MRC-5), whereas no noticeable impedance and phase changes were observed in malignant cells after increasing the aspiration with the same suction forces as shown in FIGS. 10C and 10D.

The suction forces during cell aspiration resulted in different lengths of the cell that flowed into the pipette (Lp) due to the mechanical properties of each individual cell. The Lp value was determined from microscopy images. Table 1 shows the Lp (μm) values and corresponding changes in electrical responses (electrical impedance (k$\Omega$) and phase ($\theta$)) for each single cell that was aspirated by three increasing various suction forces of F1, F2 and F3. The data shows that changes in the electrical parameters initiated from mechanical aspiration in healthy lung cells (MRC-5) were about 10 times higher than those of aspirated cancerous cells (QU-DB). These results suggest that bioelectrical properties of a healthy cell have a strong correlation with its mechanical function.

Furthermore, the effects of cancerous transformation and cell aspiration on actin microfilament distribution on control and stretched MRC-5 and QU-DB cell samples were assessed by inverted confocal microscopy. Prior to imaging, cells were fixed in about 4% formaldehyde for about 15 min and permeabilized in PBS (with the concentration of about 1%) for about 5 min to 10 min at room temperature. Then, all samples were washed and stained with the phalloidin-FITC conjugate (Green)) and incubated for about 30 min to 45 min. The cell nuclei were stained with propidium iodide (PI). The Leica Application Suite Advanced Fluorescence (LAS AF) software (Leica Microsystems) was utilized to analyze the confocal microscopy images.

Figure 11A:
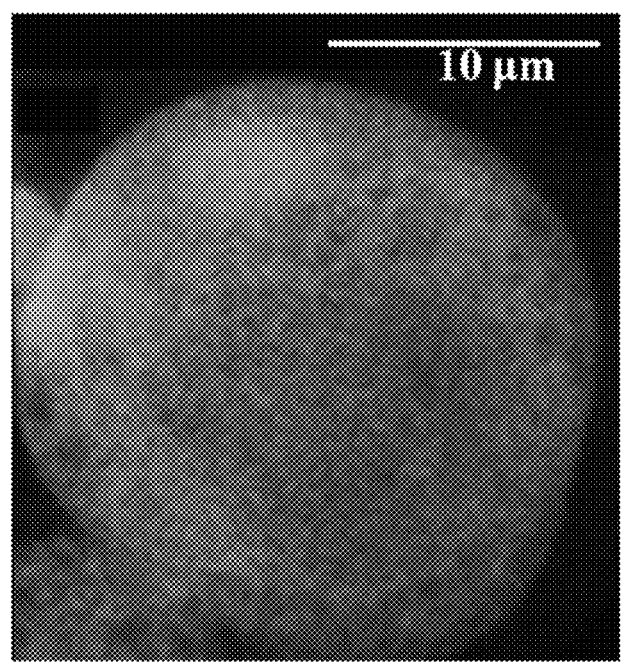
FIG. 11A illustrates a confocal microscope image of an example of a control MRC-5 cell before mechanical aspiration, consistent with one or more exemplary embodiments of the present disclosure.
Figure 11B:
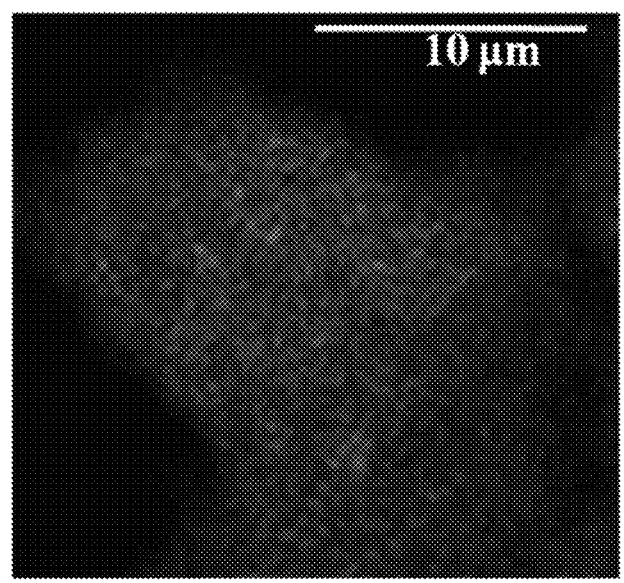
FIG. 11B illustrates a confocal microscope image of an example of a MRC-5 cell after mechanical aspiration, consistent with one or more exemplary embodiments of the present disclosure.
Figure 11C:
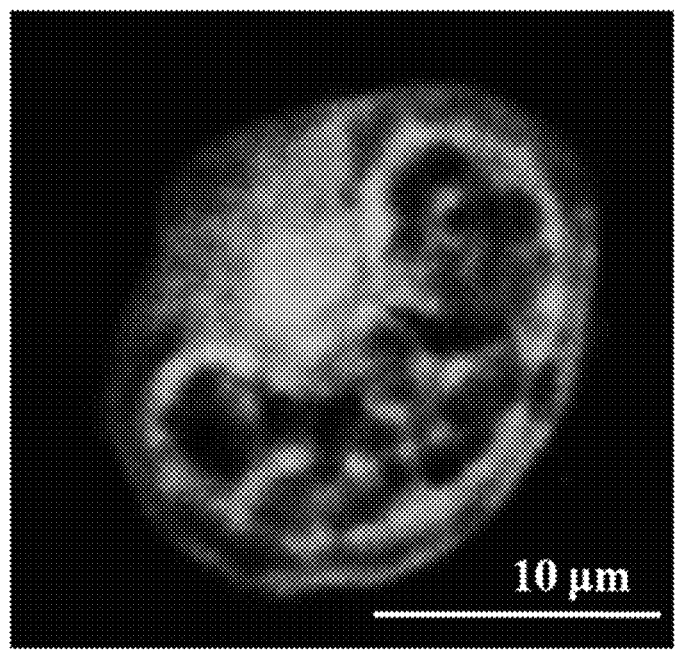
FIG. 11C illustrates a confocal microscope image of an example of a control QU-DB cell before mechanical aspiration, consistent with one or more exemplary embodiments of the present disclosure.
Figure 11D:
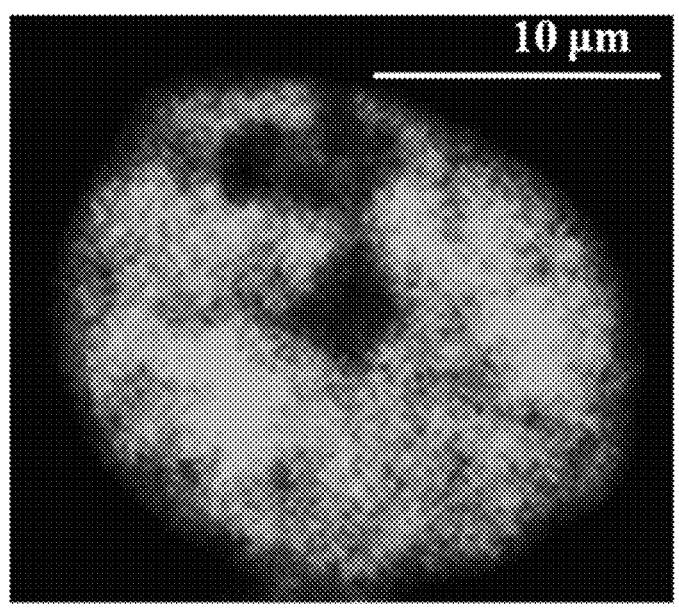
FIG. 11D illustrates a confocal microscope image of an exemplary QU-DB cell after mechanical aspiration, consistent with one or more exemplary embodiments of the present disclosure.

FIG. 11A shows a confocal microscope image of a control MRC-5 cell before aspiration, while a confocal microscope image of an aspirated MRC-5 cell is shown in FIG. 11B. FIGS. 11A and 11B show that the mechanical aspiration results in major alterations in the actin microfilaments for MRC-5 cell. Also, corresponding images are shown in FIGS. 11C and 11D representing confocal microscopy images of a control QU-DB cell before aspiration (FIG. 11C) and after aspiration (FIG. 11D) illustrating less alterations in cell actin microfilaments structure for a QU-DB in comparison with those alterations for MRC-5 cell. It may be concluded that cancerous transformation resulted in the rebundling of actin microfilaments during aspiration mechanism, so the mechanical properties and subsequently electrical properties of a cancerous cell would remain the same before and after cell aspirating. As a result, confocal microscopy showed the crucial role of actin microfilaments in cells that had highly reduced electromechanical behavior after metastatic progression. It showed the distinct differences in actin microfilament configurations between the control samples of healthy and malignant lung cells. The images showed that the actin microfilaments are bundled and remodeled in QU-DB cells during mechanical aspiration, while the actin microfilaments configurations of a healthy MRC-5 cell is significantly changed applying a mechanical aspiration.

Example 4

Detecting Cell Metastasis Progression

In this example, in order to elucidate the effect of metastasis progression of cancer cells on their electromechanical response, some experiments were performed on colon primary (HT-29) and progressive (SW-48) malignant cells. The colon primary or benign cells (HT-29) and colon progressive or metastatic (SW-48) malignant cells were obtained from the National Cell Bank of Iran, Pasteur Institute. Both types of cells were cultured, suspended and their electrical properties were measured before and after mechanical aspiration, identical to the methods and techniques described in connection with example 3.

Figure 12A:
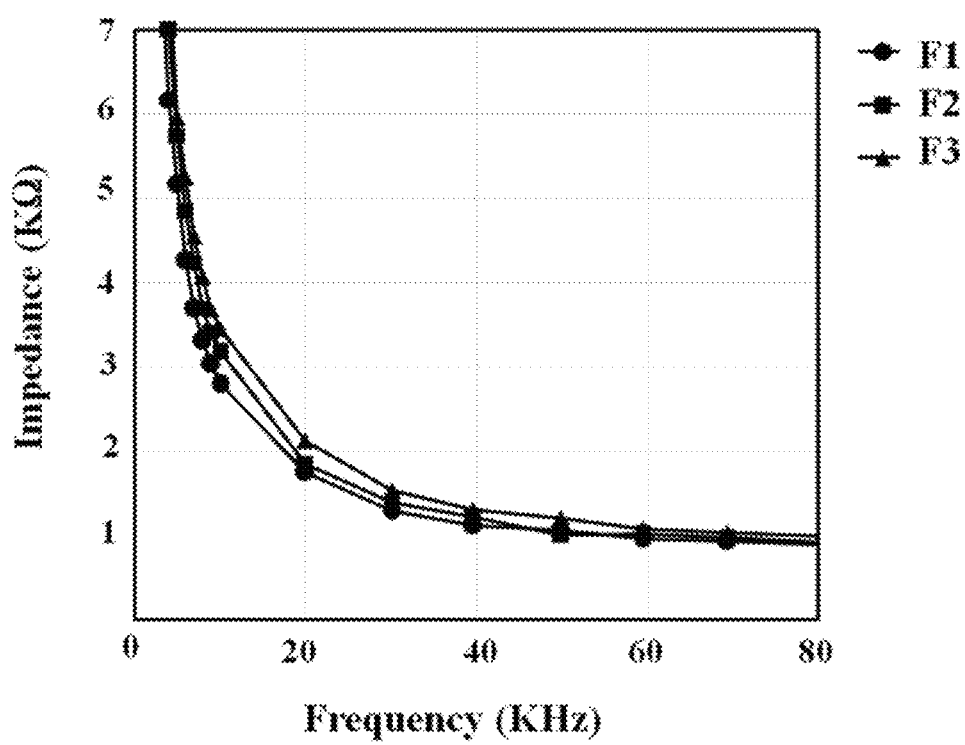
FIG. 12A is a cell impedance versus frequency curve for an exemplary aspirated HT-29 single cell with three different suction amplitudes, consistent with one or more exemplary embodiments of the present disclosure.
Figure 12B:
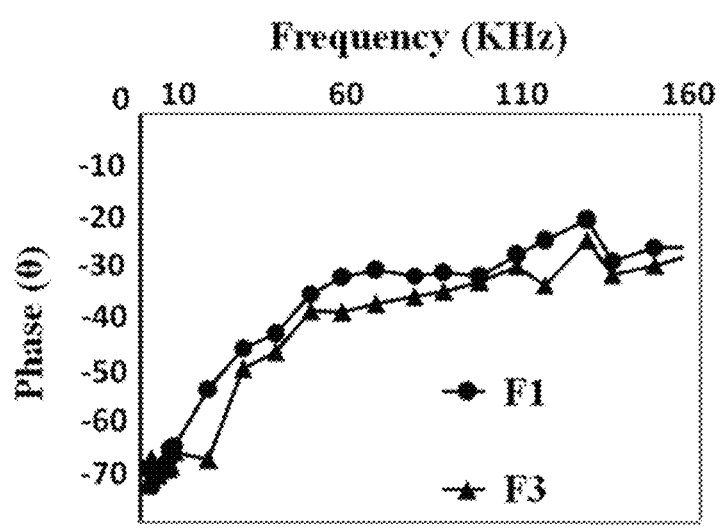
FIG. 12B is a phase response versus frequency curve for an exemplary aspirated HT-29 single cell with two different suction amplitudes, consistent with one or more exemplary embodiments of the present disclosure.
Figure 12C:
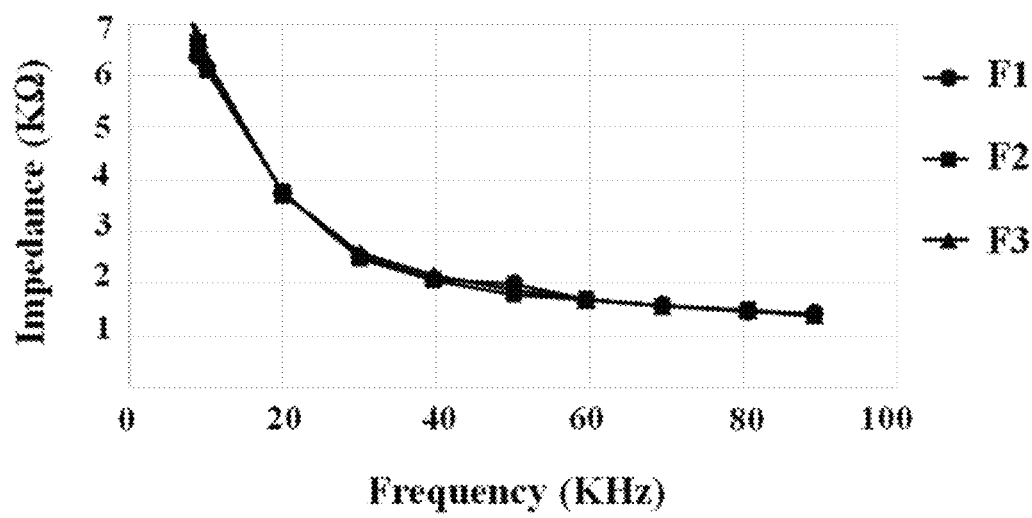
FIG. 12C is a cell impedance versus frequency curve for an exemplary aspirated SW-48 single cell with three different suction amplitudes, consistent with one or more exemplary embodiments of the present disclosure.
Figure 12D:
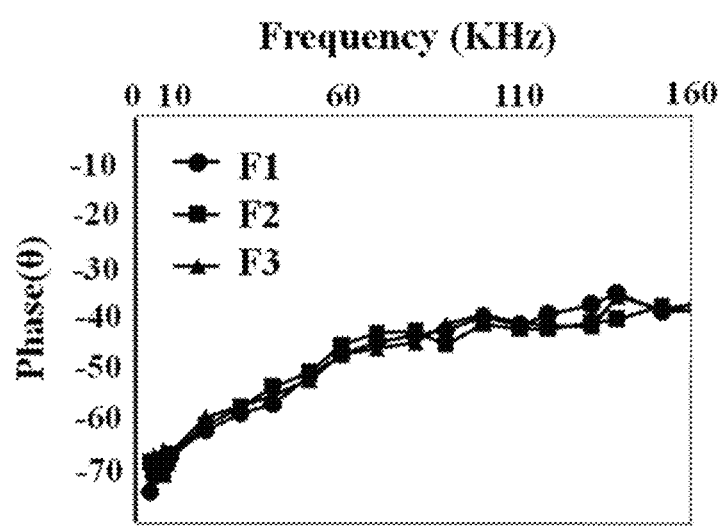
FIG. 12D is a phase response versus frequency curve for an exemplary aspirated SW-48 single cell with three different suction amplitudes, consistent with one or more exemplary embodiments of the present disclosure.

FIGS. 12A-12D show the results of the electrical measurements from aspirated HT-29 and SW-48 cells after applying three various suction forces (F1, F2 and F3) during mechanical aspiration, consistent with exemplary embodiments of the present disclosure. The representative recorded data in FIGS. 12A and 12B show an increase in the cell impedance and phase with increasing mechanical stretch amplitudes from F1 to F3 for HT-29, whereas no noticeable impedance and phase changes were observed for SW-48 after increasing the aspiration with the same suction forces as shown in FIGS. 12C and 12D.

The suction forces during cell aspiration resulted in different lengths of the cell that flowed into the pipette (Lp) due to the mechanical properties of each individual cell. The Lp value was determined from microscopy images. Table 1 shows the Lp (μm) values and corresponding changes in electrical responses (electrical impedance (kΩ) and phase (θ)) for each single cell that was aspirated by three increasing various suction forces of F1, F2 and F3. These data shows that the average impedance and phase variation of an aspirated HT-29 cell were approximately 2-fold higher than those of a SW-48 cell.

TABLE 1

Change in cell electrical parameters due to the mehanical aspiration

| Cell type | Suction force | Lp (μm) | $\Delta Imp_{ave}(\Omega)$ | $\Delta Phase_{ave}(°)$ |
|---|---|---|---|---|
| QU-DB | F1 | 4 | 190.5 | 0.73 |
|  | F2 | 6 |  |  |
|  | F3 | 8 | 88.2 | 0.52 |
| MRC-5 | F1 | 2.5 | 2776.76 | 4.01 |
|  | F2 | 4.5 |  |  |
|  | F3 | 5.8 | 2382.1 | 3.74 |
| SW-48 | F1 | 4.4 | 133.4 | 0.71 |
|  | F2 | 6.7 |  |  |
|  | F3 | 8.6 | 74.8 | 0.21 |
| HT-29 | F1 | 3.3 | 272.1 | 1.46 |
|  | F2 | 5.4 |  |  |
|  | F3 | 7.5 | 222.6 | 1.17 |

What is claimed is:

1. An electrical probe for measuring an electrical response from a biological cell, comprising:
    a tungsten microwire with a diameter less than 500 μm with a sharpened tip section, the sharpened tip section with a sharp pointed tip with a diameter of 200 nm or less;
    a catalyst layer formed on the sharpened tip section of the tungsten microwire, the catalyst layer comprising a catalyst bilayer comprising a nickel layer with a thickness in a range between 10 nm and 40 nm over a gold layer with a thickness in a range between 1 nm and 4 nm;
    an array of nanotube electrodes vertically aligned on the catalyst layer, the nanotube electrodes comprising a plurality of doped silicon nanotubes (SiNTs) comprising a long free-end silicon nanotube located on a tip of the sharpened tip section being longer than remaining SiNTs of the plurality of doped SiNTs; and
    a gold layer coated over the plurality of doped SiNTs with a thickness of 5 nm, wherein the long free-end silicon nanotube is configured to connect with and penetrate into a single biological cell.

2. The electrical probe according to claim 1, wherein the plurality of doped SiNTs comprises a plurality of doped SiNTs with phosphorus.

\* \* \* \* \*